United States Patent [19]

Pearson et al.

[11] Patent Number: 5,552,546

[45] Date of Patent: Sep. 3, 1996

[54] PROCESS FOR THE PREPARATION OF 2-ETHOXY-4,6-DIHYDROXYPYRIMIDINE

[75] Inventors: Douglas L. Pearson; Jon A. Orvik; Gary A. Roth; Carmen A. Scott; Ron B. Leng, all of Midland; Dawn L. Shiang, Sanford, all of Mich.

[73] Assignee: DowElanco, Indianapolis, Ind.

[21] Appl. No.: 282,398

[22] Filed: Jul. 28, 1994

[51] Int. Cl.$^6$ .................................................. C07D 239/02
[52] U.S. Cl. .................................................. 544/299
[58] Field of Search .................................................. 544/299

[56] References Cited

U.S. PATENT DOCUMENTS

| 3,322,526 | 5/1967 | Loux | 544/299 |
| 4,059,696 | 11/1977 | Maurer et al. | 544/232 |
| 5,010,195 | 4/1991 | Van Heertum et al. | 544/263 |
| 5,057,517 | 10/1991 | Johnston et al. | 514/254 |
| 5,250,689 | 10/1993 | Roduit et al. | 544/299 |
| 5,266,697 | 11/1993 | Escher et al. | 544/320 |
| 5,463,055 | 10/1995 | Hintermaier et al. | 544/299 |

FOREIGN PATENT DOCUMENTS

603893A1  6/1994  European Pat. Off. .

OTHER PUBLICATIONS

Basterfield, et al., *Canadian Journal of Research*, 1, 261–272 (1929).
C. J. Moye, *Australian Journal of Chemistry*, 17, 1309–1310 (1964).
Brown et al., *Journal of Applied Chemistry*, 4, 283–284 (1954).
Cox et al., *Journal of the American Chemical Society*, 63, 300–301 (1941).
Kurzer et al., *Organic Synthesis*, 4, 644–649 (1954).
Ralph H. McKee, *American Chemical Journal*, 26, No. 3, 209–213, 243–247, and 255–256 (1901).
Botta et al., *Tetrahedron*, 40, No. 17, 3313–3320 (1984).

*Primary Examiner*—Cecilia Tsang
*Attorney, Agent, or Firm*—Richard T. Knauer

[57] ABSTRACT

A salt of 2-ethoxy-4,6-dihydroxypyrimidine (DHEP) is prepared by contacting a salt of O-ethylisourea with dimethyl malonate in the presence of a methoxide base to form the salt of DHEP. The salt of DHEP can optionally be protonated with an acid to form neutral DHEP. The reaction is typically conducted in a methanol solvent at a temperature less than about 30° C. Typically, the monosodium salt of DHEP is prepared by contacting O-ethylisourea hydrochloride with dimethyl malonate in the presence of sodium methoxide and methanol solvent.

20 Claims, No Drawings

PROCESS FOR THE PREPARATION OF 2-ETHOXY-4,6-DIHYDROXYPYRIMIDINE

FIELD OF THE INVENTION

The present invention relates to a process for the preparation of 2-alkoxy-4,6-dihydroxypyrimidine by coupling O-alkylisourea with dialkyl malonate.

BACKGROUND OF THE INVENTION

2-Ethoxy-4,6-dihydroxypyrimidine (DHEP) having the Formula (I):

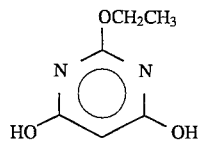

has been found to be a particularly useful intermediate for the synthesis of certain valuable herbicides used for the control of weeds in agronomic crops, such as ethoxy substituted 1,2,4-triazolo[1,5-c]pyrimidine-2-sulfonamides, as disclosed in U.S. Pat. No. 5,010,195 (Van Heertum et al.). DHEP or its monosodium salt can be converted to a 4,6-dihalo- 2-ethoxypyrimidine by treating the DHEP with a phosphorus oxyhalide compound, such as phosphorus oxychloride. Then, the 4,6-dihalo-2-ethoxypyrimidine can be treated with hydrazine hydrate and triethylamine to form a 2-ethoxy-6-halo- 4-hydrazinopyrimidine compound. The latter reaction can be carried out in water or in an organic solvent, such as acetonitrile, at a temperature of between about 0° C. and 40° C. using a slight excess of hydrazine hydrate. The 2-ethoxy-6-halo- 4-hydrazinopyrimidine compound can, if desired, be recovered by adding water to promote precipitation and then recovering the precipitate by filtration, centrifugation, or extraction. The above-referenced U.S. Pat. No. 5,010,195, which is incorporated in its entirety herein by reference, teaches how to make useful herbicide compounds from 2-ethoxy- 6-halo-4-hydrazinopyrimidine compounds.

One method taught in the art for making the 2-methoxy analog of DHEP is disclosed by S. Basterfield and E. C. Powell in *Canadian Journal of Research*, vol. 1, pp. 261–272 (1929). In this article, Basterfield and Powell describe the synthesis of a number of 2-alkoxypyrimidine derivatives, including 2-methoxy-4,6-dihydroxypyrimidine (DHMP). DHMP is prepared by condensing O-methylisourea with dimethyl malonate. Although a 75% of theoretical yield is reported in the article, the theoretical yield requires consumption of 2 equivalents of O-methylisourea to form 1 equivalent of the O-methylisourea salt of DHMP. Thus, the reported 75% yield means that 0.75 moles of DHMP salt are formed for every 2 moles of O-methylisourea utilized. The O-methylisourea is prepared by first preparing and isolating the hydrochloride salt of O-methylisourea, then neutralizing this salt with potassium hydroxide in ether to form neutral O-methylisourea, which is apparently isolated as well. At page 262 of their article, Basterfield and Powell reference the unpublished observations of Stieglitz and Basterfield, who found that O-ethylisourea can be condensed with dimethyl malonate in the absence of a base and of a solvent to obtain the O-ethylisourea salt of 2-ethoxybarbituric acid, i.e., a salt of DHEP.

A second method for making DHMP is disclosed by C. J. Moye in *Australian Journal of Chemistry*, vol. 17, pp. 1309–1310 (1964). Moye teaches condensing O-methylisourea hydrogen methyl sulfate with diethyl malonate in a methanol solvent to make DHMP. Three equivalents of sodium methoxide are used as a base to effect the condensation (two equivalents are necessary to neutralize the O-methylisourea salt and one equivalent is used to drive the condensation reaction). The methanol and sodium methoxide have the same methoxy moiety as the O-methylisourea compound and the desired product (DHMP).

SUMMARY OF THE INVENTION

The present invention concerns processes for making 2-alkoxy-4,6-dihydroxypyrimidines with an O-alkylisourea salt, a dialkyl malonate, and an alkoxide base. The alkoxide base need not have the same alkoxy moiety as the O-alkylisourea salt and the desired 2-alkoxy-4,6-dihydroxypyrimidine product. In particular, the invention relates to a process for preparing a salt of 2-ethoxy-4,6-dihydroxypyrimidine, comprising contacting a salt of O-ethylisourea with dimethyl malonate in the presence of a methoxide base and optionally further comprising protonating the salt of 2-ethoxy-4,6-dihydroxypyrimidine obtained with an acid to form neutral 2-ethoxy-4,6-dihydroxypyrimidine.

The reaction is typically conducted in a methanol solvent at a temperature less than about 30° C., and the methoxide base is typically sodium methoxide. A typical salt of 2-ethoxy-4,6-dihydroxypyrimidine (DHEP) produced by the above condensation reaction is the monosodium salt of DHEP, which has the following Formula (II):

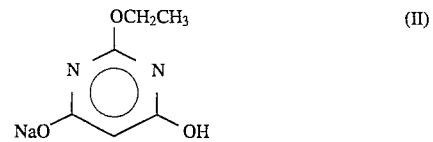

It has been discovered that the process of the invention can produce surprisingly high yields of the salt of DHEP. Surprisingly low amounts of DHMP by-product are produced in the reaction even though a methoxide base and optional methanol solvent are used. The use of sodium methoxide instead of sodium ethoxide also results in considerable raw materials cost savings in making the monosodium salt of DHEP. Further, the process uses less isourea than the Basterfield and Powell process because isourea is not tied up in forming the salt of the desired pyrimidine product.

DETAILED DESCRIPTION OF THE INVENTION

Suitable salts of O-ethylisourea for use in the condensation reaction of the invention include salts of O-ethylisourea hydrogen sulfate, hydrogen ethyl sulfate, and hydrochloride. The hydrochloride salt is often preferred. In carrying out the process of the invention, it is often preferred to prepare the O-ethylisourea salt in solution and use it without recovery. The following method of preparation is often employed. Hydrogen chloride gas is sparged into chilled anhydrous ethanol to form an ethanolic hydrogen chloride solution. The weight ratio of hydrogen chloride gas to ethanol is often about 1:4, resulting in ethanolic hydrogen chloride solutions comprising approximately 20 weight percent hydrogen chloride. Next, anhydrous cyanamide and this ethanolic hydrogen chloride solution can be added to a reactor in amounts such that the cyanamide and hydrogen chloride are present in approximately equimolar amounts. An exothermic reaction takes place and cyanamide hydrochloride is formed.

The reactants can then be heated to about 75° C. for about 15 to 20 minutes so that the cyanamide hydrochloride and ethanol react to form an ethanolic solution of O-ethylisourea hydrochloride.

If desired, the anhydrous cyanamide can be prepared by obtaining an aqueous solution of cyanamide (typically sold commercially as a 50 weight percent solution) and then distilling substantially all of the water out of the solution, typically by heating the solution and/or applying a vacuum. It may be helpful to sparge nitrogen into the bottom of the vessel holding the aqueous solution to aid in stripping water from the cyanamide. This method of preparation is often desirable because aqueous cyanamide is much less expensive than anhydrous cyanamide. Also, aqueous cyanamide is easier to handle and has better stability than anhydrous cyanamide and is a commodity chemical rather than a specialty chemical.

The O-ethylisourea hydrochloride solution prepared as described above can then be used in the condensation reaction by either cooling or heating the solution to the temperature at which the condensation reaction is to take place. Then, the dimethyl malonate and methoxide base (typically employed as a 25 weight percent solution in methanol) are added to the O-ethylisourea hydrochloride solution. The resulting slurry is then held at the desired condensation reaction temperature for the desired amount of time. The slurry can be sampled at various times to determine the amount of the salt of DHEP present in the slurry. This same procedure is followed if a different salt of O-ethylisourea is used rather than the hydrochloride, e.g., a hydrogen sulfate salt of O-ethylisourea.

The condensation reaction can be performed using near stoichiometric amounts of reagents, although dimethyl malonate and the methoxide base are preferably used in excess. The stoichiometric amount of the methoxide base is 2 equivalents for each equivalent of hydrochloride employed since 1 equivalent of the methoxide base is needed to neutralize each equivalent of hydrochloride and 1 equivalent is needed to drive the condensation reaction to completion. If a hydrogen sulfate salt of O-ethylisourea is used rather than the hydrochloride salt, the stoichiometric amount of the methoxide base is 3 equivalents for each equivalent of hydrogen sulfate employed since 2 equivalents of the methoxide base are needed to neutralize each equivalent of hydrogen sulfate and 1 equivalent is needed to drive the condensation reaction to completion.

The reaction is generally performed in one or more organic solvents that are inert to the reaction conditions. Methanol is typically used as a solvent because the methoxide base utilized in the condensation reaction is typically obtained in the form of a methanolic solution.

The condensation reaction is typically carried out with anhydrous reagents. The presence of water in the condensation reaction mixture leads to undesired side reactions and the formation of barbituric acid as a by-product.

The condensation reaction is carried out under suitable reaction conditions. The term "suitable reaction conditions" is used herein to denote a pressure and temperature at which the condensation reaction can proceed substantially to completion. Although pressure is not believed to be a critical parameter, the condensation reaction is typically carried out at about atmospheric pressure. Although the reaction can generally be carried out at a temperature between about 0° C. and the reflux temperature of the reaction mixture, it was discovered that the reaction should preferably be conducted at a temperature of between about 0° C. and about 30° C. and most preferably between about 10° C. and about 30° C. to minimize the amount of DHMP by-product formed. In other words, it was discovered that higher temperatures during the condensation reaction (i.e., temperatures near the reflux temperature of the reaction mixture) generally result in shorter reaction times but lower yields of DHEP due to a greater conversion to the DHMP by-product. At temperatures less than about 30° C., surprisingly high yields of DHEP can be obtained with a much lower conversion to the DHMP by-product although reaction times are generally longer.

Typically, the methoxide base used in the condensation reaction of the invention is an alkali metal methoxide. Sodium methoxide is a particularly preferred alkali metal methoxide.

A salt of DHEP precipitates out of the reaction mixture during the condensation reaction and can be recovered or employed as an intermediate in a subsequent chemical process without recovery and/or purification. If the methoxide base used in the condensation reaction is sodium methoxide, the salt of DHEP produced by the reaction is the monosodium salt of DHEP. If it is desired to isolate the sodium salt of DHEP, the following steps are preferably taken. After the condensation reaction of dimethyl malonate and sodium methoxide proceeds substantially to completion, the reaction mixture can be distilled at about 64° C. to distill methanol from the reaction mixture, and ethanol can be added to the mixture to enhance the precipitation of the sodium salt of DHEP out of the mixture. This solvent exchange step is carried out because the sodium salt of DHEP is much more soluble in methanol than ethanol. Next, the precipitate of the sodium salt of DHEP is filtered from the organic solution to produce a wetcake of the sodium salt of DHEP. This wetcake can be dried to obtain a dried solid comprising the sodium salt of DHEP.

If it is desired to isolate neutral DHEP rather than a salt thereof, water and an acid, e.g., hydrochloric, acetic, or preferably formic acid, can be added to the slurry after the condensation reaction takes place to form a precipitate comprising neutral DHEP. The precipitate can then be filtered, or filtered after distilling alcohols from the slurry. The insoluble solids can then be washed with water or other suitable solvent and then dried.

Another process option can be used to produce either DHEP or its salt as a slurry in an external liquid (solvent) so that isolation by filtration and drying is not necessary. The reactants and conditions used are similar to those previously described. The liquid, preferably a high boiling point (about 200° C. or greater), inert, organic liquid such as ALKYLATE™ 215 solvent (a solvent available from the Monsanto Company, the solvent comprising a mixture of $C_{11}$–$C_{16}$ alkylbenzenes and having a boiling point of 265°–300° C.) can be introduced as early as the aqueous cyanamide drying step and can be used to keep reaction mixtures fluid while distilling lower boiling point solvents from reaction mixtures such as ethanol after the isourea is prepared, and methanol and dimethyl malonate after the condensation reaction is conducted. This has the advantage of allowing an excess of the relatively expensive dimethyl malonate to be used to increase the reaction rate while recycling the dimethyl malonate for subsequent use. Following the methanol and dimethyl malonate removal, the slurry can be safely used in the subsequent chlorination reaction without further isolation or purification of the pyrimidine product, thus significantly simplifying the process equipment requirements. This aspect is particularly significant in conducting a continuous manufacturing process rather than batch operations.

The following examples are presented to illustrate the invention. They should not be construed as limiting the scope of the invention.

All solvents and reagents were obtained from commercial suppliers without further purification, except as noted. A jacketed, 600 mL reactor equipped with an overhead stirrer and a cold water condenser/claisen head apparatus was used in each of the Examples set forth below.

EXAMPLES

Example 1—Preparation of the Monosodium Salt of DHEP

A nitrogen-purged round bottom flask equipped with an overhead stirrer and a dry ice condenser was charged with about 400 g (grams) of toluene-denatured anhydrous ethanol. An ice bath was used to chill the ethanol to less than 10° C., and anhydrous hydrogen chloride gas (about 100 g) was sparged into the ethanol via a glass dip tube over the course of about 3 hr (hours) while maintaining the temperature at about 10° C. The resulting ethanolic hydrogen chloride solution was titrated using 0.1N (Normal) sodium hydroxide and found to contain 19.8 weight percent (wt. %) of hydrogen chloride.

Anhydrous cyanamide (21.0 g, 0.5 mol (moles)) and the above ethanolic hydrogen chloride solution (92.5 g solution, 19.8 wt. % HCl, 0.50 mol HCl) were charged to the jacketed reactor with stirring. An exothermic reaction raised the pot temperature of the reactor to 47° C. and a white slurry formed. The white slurry was heated, and an exothermic reaction began when the pot temperature reached 55° C. The pot temperature continued rising as a result of the exothermic reaction and peaked at 82° C. The bath temperature was then raised to 75° C. and the cyanamide hydrochloride reacted with the ethanol for 15 minutes to form an ethanolic solution of O-ethylisourea hydrochloride.

The bath temperature was then lowered to 50° C. After another 30 min (minutes), the pot temperature had cooled to 57° C., and dimethyl malonate (85.6 g, 0.65 mol) and a 25 wt. % solution of sodium methoxide in anhydrous methanol (227.7 g solution, 56.9 g sodium methoxide, 1.05 mol sodium methoxide) were added to the reactor all at once through a funnel while stirring the reagents in the pot. The dimethyl malonate and sodium methoxide formed a white precipitate in the funnel. Most of the white precipitate in the funnel was flushed into the reactor with anhydrous ethanol (20 mL), and the pot was heated to 65° C. After 6 hr, 25 min reaction time, the pot temperature was reduced from 65° C. to 20° C., and the reaction mixture was allowed to sit overnight (18 hr, 45 min) with stirring.

The resulting white slurry in the pot was filtered, leaving a white wetcake and a milky filtrate which was used to flush the reactor pot and then refiltered over the wetcake. The second filtrate was an off-white solution. The wetcake was vacuum dried overnight at 75° C., resulting in a white, sugar-like product (96.3 g) which was ground up with a mortar and pestle to a fine powder. A sample of this powder was dissolved in water, analyzed by high performance liquid chromatography (HPLC), and compared to the chromatogram of an aqueous sample having a known concentration of DHEP. The experimental sample was found to contain 52.5 g of DHEP (0.34 mol, 67.2% of theoretical yield). The content of DHMP by-product in the experimental sample was determined in an analogous manner to be 6.2 g (0.04 mol, 8.7% of theoretical yield). The second filtrate obtained from the filtration above was also analyzed by HPLC in an analogous manner and found to contain amounts of DHEP and DHMP resulting in a yield loss of 7.7% DHEP and a yield loss of 7.5% DHMP. Thus, the total accountable yields were 74.9% for DHEP and 16.2% for DHMP by-product. The yield amounts referred to in this paragraph were calculated for the neutral forms of the pyrimidine products since the pyrimidine salts of the aqueous samples analyzed by HPLC were protonated to neutral pyrimidines in the column of the HPLC apparatus during the HPLC analysis.

Example 2—Preparation of the Monosodium Salt of DHEP

Anhydrous cyanamide (21.0 g, 0.5 mol) and an ethanolic hydrogen chloride solution (98.1 g solution, 18.6 wt. % HCl, 0.50 mol HCl) were charged to the jacketed reactor with stirring. An exothermic reaction raised the pot temperature of the reactor to 50° C. The resulting white slurry was then heated. The solute of the white slurry went into solution and an exothermic reaction began when the pot temperature reached 55° C. The pot temperature continued rising as a result of the exothermic reaction and peaked at 83° C. The bath temperature was then raised to 75° C. and maintained for 20 minutes to form an ethanolic solution of O-ethylisourea hydrochloride.

The pot temperature was then cooled to 27° C. during the next 35 min, and dimethyl malonate (83.0 g, 0.63 mol) and a 25 wt. % solution of sodium methoxide in anhydrous methanol (227.2 g solution, 56.8 g sodium methoxide, 1.05 mol sodium methoxide) were added to the reactor all at once with stirring. The pot temperature increased to 29° C. as the clear solution became a white slurry. The reaction mixture was allowed to sit overnight with stirring at about 25° C. for a total condensation reaction time of 18 hr, 45 min.

The resulting white slurry in the pot was cooled to 20° C. and filtered, leaving a white wetcake and a filtrate which was used to flush the reactor pot and then refiltered over the wetcake. The wetcake was vacuum dried overnight at 75° C., resulting in a white solid (94.7 g) which was ground up with a mortar and pestle to a fine powder. This powder was assayed by HPLC as described in Example 1 and found to contain about 52.4 g of DHEP (0.34 mol, 67.2% of theoretical yield) and 1.9 g of DHMP by-product (0.01 mol, 2.7% of theoretical yield). The second filtrate was found to contain amounts of DHEP and DHMP resulting in a yield loss of 17.2% DHEP and a yield loss of 3.2% DHMP. Thus, the total accountable yields were 84.4% for DHEP and 5.9% for DHMP by-product.

Example 3—Preparation of the Monosodium Salt of DHEP

Anhydrous cyanamide (21.0 g, 0.5 mol) and an ethanolic hydrogen chloride solution (90 g solution, 21.2 wt. % HCl, 0.52 mol HCl) were charged to the jacketed reactor with stirring. An exothermic reaction raised the pot temperature of the reactor from 20° C. to 46° C., at which temperature a clear solution was present. As the pot temperature was cooled to 30° C., a white slurry formed. The bath temperature was then raised to 60° C. An exothermic reaction began when the pot temperature reached 50° C. The pot temperature continued rising as a result of the exothermic reaction and peaked at 82° C., and a clear solution resulted. The bath temperature was then raised to 70° C. and maintained for 20 minutes to form an ethanolic solution of O-ethylisourea hydrochloride.

The pot temperature was then cooled to 25° C. during the next 20 min, and dimethyl malonate (66.2 g, 0.50 mol) and a 25 wt. % solution of sodium methoxide in anhydrous methanol (226.8 g solution, 56.7 g sodium methoxide, 1.05 mol sodium methoxide) were added to the reactor all at once with stirring. The pot temperature increased to 29° C. as the clear solution became a white slurry. The reaction mixture was allowed to sit overnight with stirring at about 25° C. for a total condensation reaction time of 23 hr, 45 min.

The resulting white slurry in the pot was poured into a round bottom flask and the slurry residue remaining in the pot was washed into the flask with anhydrous ethanol (108 g). The flask was then attached to the base of an Oldershaw distillation column having approximately 25 trays. A fractional distillation was conducted to remove the most volatile solvents from the flask. During the distillation, the reflux ratio was initially 1 and ended at 20, while the temperature of the materials remaining in the flask (the bottoms) started at about 70° C. and ended at about 80° C. At the end of the distillation, the flask contained a white slurry which was filtered, leaving a white wetcake and a light yellow filtrate. The wetcake was washed three times with anhydrous ethanol (about 110–120 g of ethanol each wash), filtered after each wash, and vacuum dried overnight at 75° C., resulting in a white solid (101.8 g) which was ground up with a mortar and pestle to a fine powder. This powder was assayed by HPLC as described in Example 1 and found to contain about 56.7 g of DHEP (0.36 mol, 72.6 % of theoretical yield) and 3.8 g of DHMP by-product (0.03 mol, 5.3% of theoretical yield). The first, second, third, and fourth filtrates were found to contain amounts of DHEP and DHMP resulting in a yield loss of 7.6% DHEP and a yield loss of 2.7% DHMP. Thus, the total accountable yields were 80.2% for DHEP and 8.0% for DHMP by-product.

Example 4—Preparation of the Monosodium Salt of DHEP

Anhydrous cyanamide (21.0 g, 0.5 mol) and an ethanolic hydrogen chloride solution (88.2 g solution, 20.7 wt. % HCl, 0.50 mol HCl) were charged to the jacketed reactor with stirring. An exothermic reaction raised the pot temperature of the reactor from 14° C. to 51° C., at which temperature a clear solution was present. The bath temperature was then raised to 60° C. An exothermic reaction raised the pot temperature to 82° C. The bath temperature was then raised to about 70°–71° C. and maintained for 20 min to form an ethanolic solution of O-ethylisourea hydrochloride.

The pot temperature was then cooled to 10° C., and dimethyl malonate (83.0 g, 0.63 mol) was added with stirring, but no change in the clear solution resulted. Then, a 25 wt. % solution of sodium methoxide in anhydrous methanol (229 g solution, 57.2 g sodium methoxide, 1.06 mol sodium methoxide) was added to the reactor all at once with stirring and the clear solution changed to a white slurry as the pot temperature exothermed to about 20° C. in a matter of seconds. The pot was cooled to about 10° C. during the next 30 min, and the reaction mixture was allowed to sit with stirring at about 10° C. for a total condensation reaction time of 45 hr, 40 min.

The resulting white slurry in the pot was filtered, leaving a white wetcake which was washed twice with anhydrous ethanol (about 130 g of ethanol the first wash and about 110 g of ethanol the second wash), filtered after each wash, and vacuum dried overnight at 75° C., resulting in a white solid (91.9 g) which was ground up with a mortar and pestle to a fine powder. This powder was assayed by HPLC as described in Example 1 and found to contain about 54.0 g of DHEP (0.35 mol, 69.2% of theoretical yield) and 0.6 g of DHMP by-product (0.005 mol, 0.9% of theoretical yield). The first, second, and third filtrates were found to contain amounts of DHEP and DHMP resulting in a yield loss of 19.6% DHEP and a yield loss of 2.9% DHMP. Thus, the total accountable yields were 88.8% for DHEP and 3.8% for DHMP by-product.

Various modifications and alterations of this invention will be apparent to those skilled in the art without departing from the scope and spirit of this invention.

What is claimed is:

1. A process for preparing a salt of 2-ethoxy-4,6-dihydroxypyrimidine, comprising contacting a salt of O-ethylisourea with dimethyl malonate in the presence of a methoxide base and optionally further comprising protonating the salt of 2-ethoxy-4,6-dihydroxypyrimidine obtained with an acid to form neutral 2-ethoxy-4,6-dihydroxypyrimidine.

2. The process of claim 1 wherein the reaction is conducted at a temperature between about 0° C. and about 30° C.

3. The process of claim 1 wherein the reaction is conducted in the presence of a methanol solvent.

4. The process of claim 1 wherein the methoxide base is an alkali metal methoxide.

5. The process of claim 4 wherein the alkali metal methoxide is sodium methoxide.

6. The process of claim 1 wherein the salt of O-ethylisourea is selected from the group consisting of O-ethylisourea hydrochloride, hydrogen ethyl sulfate, and hydrogen sulfate salts of O-ethylisourea.

7. The process of claim 6 wherein the salt of O-ethylisourea is O-ethylisourea hydrochloride.

8. The process of claim 1 further comprising protonating the salt of 2-ethoxy-4,6-dihydroxypyrimidine obtained with an acid to form neutral 2-ethoxy-4,6-dihydroxypyrimidine.

9. The process of claim 1 wherein the reaction is conducted in the presence of a high boiling point organic solvent.

10. The process of claim 9 wherein the high boiling point organic solvent comprises a mixture of $C_{11}$–$C_{16}$ alkylbenzenes.

11. A process for preparing the monosodium salt of 2-ethoxy-4,6-dihydroxypyrimidine, comprising contacting O-ethylisourea hydrochloride with dimethyl malonate in the presence of sodium methoxide and optionally further comprising protonating the monosodium salt of 2-ethoxy-4,6-dihydroxypyrimidine obtained with an acid to form neutral 2-ethoxy-4,6-dihydroxypyrimidine.

12. The process of claim 11 wherein the reaction is conducted at a temperature between about 0° C. and about 30° C.

13. The process of claim 11 wherein the reaction is conducted in the presence of a methanol solvent.

14. A process for preparing 2-ethoxy-4,6-dihydroxypyrimidine, comprising:

(a) contacting O-ethylisourea hydrochloride with dimethyl malonate in the presence of sodium methoxide and methanol solvent to form the monosodium salt of 2-ethoxy-4,6-dihydroxypyrimidine; and (b) protonating the monosodium salt of 2-ethoxy-4,6-dihydroxypyrimidine with an acid to form neutral 2-ethoxy-4,6-dihydroxypyrimidine.

15. A process for preparing a salt of 2-ethoxy-4,6-dihydroxypyrimidine, comprising contacting a solution of an O-ethylisourea salt with dimethyl malonate in the presence of a methoxide base and methanol solvent and optionally further comprising protonating the salt of 2-ethoxy-4,6-dihydroxypyrimidine obtained with an acid to form neutral 2-ethoxy-4,6-dihydroxypyrimidine.

16. The process of claim 15 wherein the solution of O-ethylisourea salt is an ethanolic solution.

17. The process of claim 15 wherein the solution of O-ethylisourea salt comprises O-ethylisourea hydrochloride and is prepared by reacting anhydrous cyanamide with an ethanolic hydrogen chloride solution to form cyanamide hydrochloride, and then reacting the cyanamide hydrochloride with ethanol to form O-ethylisourea hydrochloride in solution.

18. The process of claim 17 wherein the anhydrous cyanamide is prepared by obtaining an aqueous solution of cyanamide and distilling substantially all of the water out of the aqueous solution to form anhydrous cyanamide.

19. The process of claim 14 wherein the reaction of O-ethylisourea hydrochloride with dimethyl malonate is conducted at a temperature between about 0° C. and about 30° C.

20. The process of claim 15 wherein the reaction of O-ethylisourea hydrochloride with dimethyl malonate is conducted at a temperature between about 0° C. and about 30° C.

* * * * *